United States Patent [19]

Wilson

[11] Patent Number: 5,197,967
[45] Date of Patent: Mar. 30, 1993

[54] TREPHINE INSTRUMENT AND METHOD FOR CUTTING ANNULAR HOLES

[75] Inventor: Frank Wilson, Prospect Park, Pa.

[73] Assignee: Synthes (U.S.A.), Paoli, Pa.

[21] Appl. No.: 679,259

[22] Filed: Apr. 2, 1991

[51] Int. Cl.$^5$ .............................................. A61F 17/00
[52] U.S. Cl. ....................................... 606/79; 606/80
[58] Field of Search ................... 606/53, 79, 80, 81, 606/167, 170, 180, 185, 166, 168, 169, 172

[56] References Cited

U.S. PATENT DOCUMENTS

| | | | |
|---|---|---|---|
| 1,123,720 | 1/1915 | Greenfield | 606/170 X |
| 3,367,335 | 2/1968 | Ward et al. | 606/167 |
| 3,945,375 | 3/1976 | Banko | 606/170 X |
| 4,004,581 | 1/1977 | Heimke et al. | 606/170 X |
| 4,273,117 | 6/1981 | Neuhauser | 606/8 X |
| 4,517,977 | 5/1985 | Frost | 606/170 |

Primary Examiner—Robert A. Hafer
Assistant Examiner—Sam Rimell
Attorney, Agent, or Firm—Davis Hoxie Faithfull & Hapgood

[57] ABSTRACT

An improved trephine instrument for use in bone surgery comprises a tubular casing, an annular cutting face disposed on one end of the casing, and a cannulated piston mounted on a spring in the housing. The cutting face comprises a plurality of prongs spaced from each other, with thickened cutting edges at their tips. The head of the piston exends beyond the cutting face in the forward position. A flange is formed at the head of the piston. In use, a Kirschner wire is attached to the bone and inserted into the cannulation in the piston. The trephine instrument is then rotated and pressed foward to cut a bone plug.

16 Claims, 2 Drawing Sheets

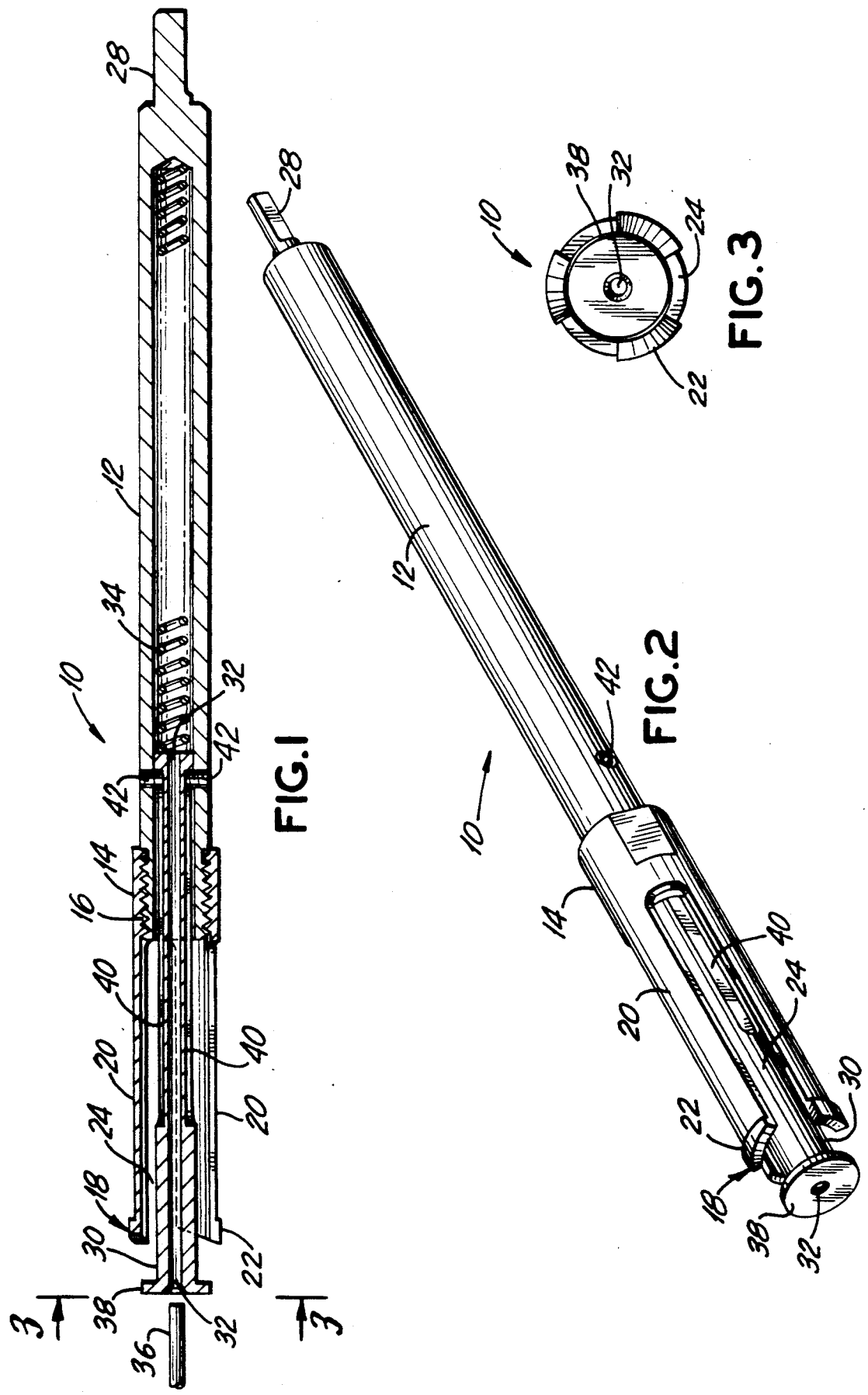

TREPHINE INSTRUMENT AND METHOD FOR CUTTING ANNULAR HOLES

FIELD OF THE INVENTION

The present invention relates to the field of plug cutting tools and methods, and particularly trephine instruments intended for use in bone surgery.

BACKGROUND OF THE INVENTION

In certain types of surgery it becomes necessary to drill an annular hole into a bone. For example, certain compression fractures can be treated by drilling an annulus into the bone in the area of the fracture and pressing the fractured section of bone into its original position. The position of the bone is then secured with a screw. This procedure is particularly useful in treating compression fractures in the bones of the leg and knee. In another application, drilling an annulus into the bone is necessary in order to harvest a plug of healthy bone for grafting into an area of bone which is damaged or diseased.

A trephine instrument which is commonly used to perform such surgery comprises an annular drill with a pointed projection in the center of the annulus. The projection typically extends 5-10 millimeters beyond the cutting face, and is used to guide the path of the drill. It does not always do so satisfactorily, however, and the drill may deviate from its intended path. The projection can also injure soft tissue beyond the bone, such as brain tissue, arteries, or nerves. In addition, it is often difficult to remove the drill without removing all or part of the bone plug with it, since the plug tends to bind to the instrument.

Another type of trephine instrument currently in use has an annular cutting face, but does not employ a projection in the center of the cutting face. This instrument is similar to annular drills used in carpentry. The problem of deviation from the desired path is exacerbated in this type of instrument, since the drill is not guided by anything except the cutting face itself. Cleanly removing the instrument from the bone also continues to be a problem.

SUMMARY OF THE INVENTION

It is therefore an object of the present invention to provide a trephine instrument which overcomes the deficiencies of the prior art.

It is a further object of the invention to provide a trephine instrument which is accurately guided through the material being cut.

It is a further object of the invention to provide a trephine instrument which minimizes damage to surrounding tissue.

It is a further object of the invention to provide a trephine instrument which can be cleanly withdrawn after cutting.

In accordance with a first aspect of the invention, a trephine instrument comprises a housing, having a cutting face at a first end, a piston disposed in the housing, adapted for linear movement inwardly and outwardly of the first end of the housing, a cannulation in the piston adapted to accommodate guide means, said guide means preventing substantial deviation of the trephine instrument from its path during cutting, and resilient means urging the piston toward the first end of the housing.

In accordance with a second aspect of the invention, a trephine instrument comprises a housing, a cutting face at a first end of the housing, and a piston movably disposed in the housing coaxial with the cutting face. The cutting face comprises a plurality of extensions protruding from the housing, which are spaced from each other and are arranged approximately in a circle, to cut an annulus into material in contact with the cutting face when the trephine instrument is rotated. A flange, of approximately the same diameter as the inner diameter of the extensions, is disposed at the head of the piston to bear against the bone inside the cutting face.

In accordance with a third aspect of the invention, a method of cutting an annular hole into a bone with a trephine instrument comprising a housing with a cutting face on a first end and a cannulated piston resiliently disposed within the housing and adapted for linear movement relative to said cutting face, comprises the steps of securing a guide to the bone, placing the trephine instrument over the guide through the cannulation in the piston, rotating the trephine instrument and pressing it into the bone, thereby causing the cutting face to cut a bone plug, the bone plug pressing the piston into the housing as the cutting proceeds, and removing the trephine instrument, the pressure of the piston against the bone plug helping to remove the trephine instrument cleanly.

Specifically, and in a preferred embodiment, a trephine instrument for use in bone surgery comprises a tubular casing, with a cutting face disposed on a first end of the casing. The cutting face comprises a plurality of prongs spaced from each other and arranged in a circle, each prong having a thickened cutting edge. Means for attachment of a rotating device is disposed on a second end of the casing. A piston is resiliently mounted in the casing coaxial with the cutting face, and is adapted for linear movement inwardly and outwardly of the cutting face. The piston has a widened head which extends beyond the cutting face. The piston has a cannulation, which is adapted for placement over a guide, such as a Kirschner wire, secured in the bone. One or more grooves are disposed at the side of the piston, which cooperate with protrusions such as screws extending from the side of the casing. The cooperation of the grooves and protrusions limit the movement of the piston relative to the casing.

BRIEF DESCRIPTION OF THE DRAWINGS

FIG. 1 is a side view in cross section of an example of a trephine instrument according to the invention.

FIG. 2 is a perspective view of the trephine instrument of FIG. 1.

FIG. 3 is a view along line 3—3 of FIG. 1.

DETAILED DESCRIPTION OF THE INVENTION

Figure 4:
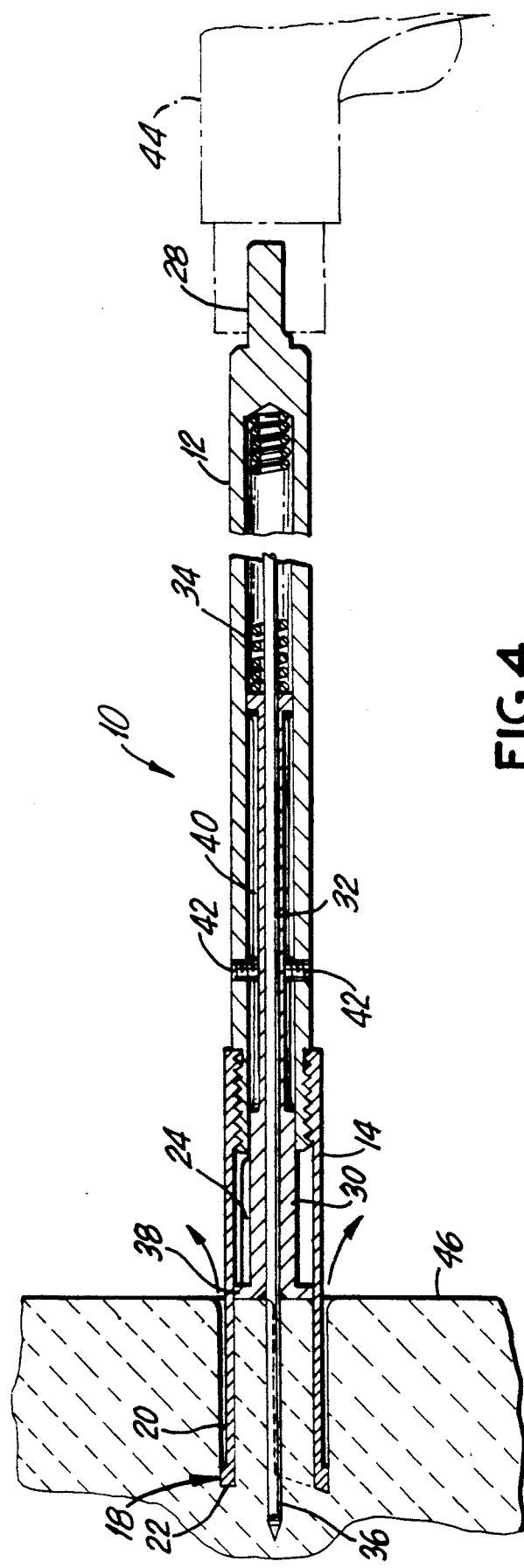
FIG. 4 is a side view in cross section of the trephine instrument of FIG. 1 during use.

Referring first to FIGS. 1-3, a trephine instrument 10 according to the invention comprises a tubular housing or casing 12, to which is attached a cutting head 14. The term "trephine instrument" as used herein signifies any apparatus which drills or cuts an annulus. The cutting head 14 is screwed onto one end of the tubular casing 12 on threads 16. The head 14 has a cutting face 18 at its free end which is formed from three prongs 20, each prong having a thickened cutting edge 22 at its tip. The cutting edges 22 are thickened so that the body of the cutting head 14 and casing 12 will not contact the bone during cutting. This is desired because the friction arising from contact creates heat, which kills the bone tissue surrounding the trephine instrument 10 (a phenomenon called "heat necrosis"). Heat necrosis prolongs healing time, and complicates acceptance of a bone graft. Spaces 24 lie between the prongs 20. Spaces 24 serve to further reduce contact with the bone, to provide an escape for cut bone tissue, and to provide access for cooling liquid to the cutting head 14 during cutting.

A stud 28, for insertion into a pneumatic drill or similar rotating device, extends from the end of the casing 12 opposite the head 14.

A piston 30 having a cannulation 32 is inserted snugly into the casing 12 above a helical spring 34, which keeps the piston 30 in a forward position when the instrument 10 is not in use. The cannulation 32 is adapted to receive a rigid Kirschner wire 36 or like device during use. The head of the piston 30 protrudes slightly beyond the cutting face 18 in the forward position A flange 38 is formed at the head of the piston 30, the diameter of which approximates the inner diameter of the cutting head 14 in the area of the prongs 20. The flange 38 keeps the prongs 20 from bending toward each other under the pressure of the surrounding bone during initial drilling. The entire piston 30 may be made to be the diameter of the flange 38 if desired, but it is preferable to have only a flange for considerations of weight and size, and to allow room for debris arising from drilling.

Two grooves 40 extend along the length of the piston 30, into each of which a set screw 42 is inserted through a hole in the casing 12. The set screws 42 are placed to cooperate with the grooves 40 to limit travel of the piston 30, and cause the piston 30 to rotate as a unit with the casing 12 during use. In the forward position of the piston 30, the abutment of the screws 42 against the back end of the grooves 40 keeps the spring 34 from pushing the piston 30 out of the casing 12.

Referring now to FIG. 4, in operation of the trephine instrument 10, a Kirschner wire 36 is inserted into a bone 46 at the point at which it is desired to drill, and the instrument 10 is put into position by inserting the Kirschner wire 36 into the cannulation 32 of the piston 30. The flange 38 is pressed against the surface of the bone to be cut, and remains in that position throughout the cutting procedure. The Kirschner wire 36 guides the instrument 10 during cutting, and keeps the latter from deviating from a straight line. This is especially important in the case of a bone which does not have a flat surface, or when drilling into a bone at an angle, in which cases the instrument 10 tends to veer toward an axis normal to the surface of the bone during drilling. The depth of insertion of the Kirschner wire 36 is not important, so long as it is sufficiently anchored in the bone 46.

A pneumatic drill 44 or other rotating device is attached to the stud 28 and activated, rotating the trephine instrument 10. Since the head of the piston 30 protrudes from the cutting face 18 in the forward position, the desired rotational speed of the cutting face 18 may be reached before contacting the bone. The instrument 10 is pressed forward into the bone, and the cutting face 18 cuts an annular hole in the bone. The bone tissue debris created from the cutting action enters the spaces 24 between the prongs 20, and either stays there or exits onto the surface, as indicated by the arrows in FIG. 4. The cutting face 18 is cooled by placing saline solution or other suitable cooling liquid into the area being cut, which liquid enters the spaces 24 and works its way down to the cutting face 18.

The prongs 20 are kept from deviating during cutting by the surrounding bone 46 and the flange 38. The prongs 20 tend to move outwardly due to centrifugal force, but are prevented from doing so by the surrounding bone 46. The bone 46 also tends to push the prongs 20 inwardly, but inward movement is prevented by the flange 38 initially, and by the bone plug itself as cutting progresses.

The instrument 10 drills into the bone until the flange 38 abuts the end of the tubular casing 12. At the same time, the set screws 42 abut the forward end of the grooves 40. It will be appreciated that either of these methods of delimiting the range of movement of the piston 30 ma be used independently of the other. If a shorter distance of drilling is desired in a particular application, the movement of the instrument 10 may of course be arrested manually.

After the bone plug has been cut, the instrument 10 is withdrawn from the bone. During this movement, the flange 38 at the head of the piston 30 presses against the bone plug under the pressure of the spring 34, ensuring that the bone plug does not bind in the instrument 10, whereby the latter is cleanly withdrawn from the bone. The bone plug may then be pressed forward to repair a fracture, or may be removed by twisting the Kirschner wire 36, which breaks the end of the bone plug off the surrounding bone. The bone plug may then be grafted into another area of the body.

The trephine instrument 10 is particularly useful for operations on the knee (e.g., treating compression fractures of the tibia and femur), and for graft harvesting in the elbow and pelvic bones. However, it can be used on any bone in the body with similar effectiveness.

The foregoing description describes a particular embodiment of the invention; it is not intended to describe all possible embodiments. Modifications to the described embodiment while remaining within the scope of the invention will be apparent to those skilled in the art.

I claim:

1. A trephine instrument for cutting an annulus into a material, which is accurately guided in a pre-determined path through said material, comprising:
   a hollow housing, having a cutting head at a first end;
   a piston disposed in said housing adapted for linear movement inwardly and outwardly of said first end of said housing;
   a cannulation extending through the length of said piston to accommodate a guide wire attached to material to be cut; and
   resilient means urging said piston toward said first end of the housing to eject out material from said housing.

2. The trephine instrument of claim 1, wherein said cutting head comprises a plurality of prongs having cutting edges, and spaces between said prongs, whereby cut material accumulates in said spaces and escapes to the surface of said material through said spaces.

3. The trephine instrument of claim 1, wherein said resilient means is a spring.

4. The trephine instrument of claim 2 wherein in the area of said cutting edges said prongs have a thickness greater than their thickness at points remote from said cutting edges.

5. The trephine instrument of claim 1, further comprising a guide wire for positioning in said cannulation.

6. A trephine instrument, comprising:
a housing;
a cutting face at a first end of said housing, comprising a plurality of extensions from said housing, said extensions being spaced from each other, and arranged approximately in a circle, to cut an annulus into material in contact with said face when said trephine instrument is rotated;
a piston, movably disposed in said housing coaxial to said cutting face to move inwardly and outwardly relative to said first end of said housing; and
a flange disposed at the head of said piston, of approximately the same diameter as the inner diameter of said extensions.

7. The trephine instrument of claim 6, further comprising a cannulation in said piston, adapted for placement over a guide attached to said material to be cut.

8. A trephine instrument for use in bone surgery, which is accurately guided through the bone, and which can be cleanly withdrawn from the bone after cutting, comprising:
a tubular casing;
a cutting head disposed on a first end of said casing, comprising a plurality of prongs spaced from each other and arranged in a circle, each prong having a cutting edge which is thicker than the remainder of said prongs;
means for attachment of a rotating device, disposed on a second end of said casing;
a piston, having a widened head extending beyond said cutting head, resiliently mounted in said casing coaxial with said cutting head and adapted for linear movement inwardly and outwardly of said cutting head,
a cannulation in said piston, adapted for placement over a guide wire secured in the bone;
a groove disposed at the side of said piston; and
a protrusion extending from said casing into said groove, whereby the cooperation of said grove and said protrusion limit said movement of said piston relative to said casing.

9. A trephine instrument comprising
a housing having an end;
means on said end of said housing for cutting an annulus in selected material to leave a block of said material in said housing at said end;
a piston having a cannulation extending through the length of said piston for receiving a guide wire attached to said material; and
means for moving said piston linearly in said housing to transport cut material from said housing.

10. The trephine instrument of claim 9, wherein said means for cutting an annulus comprises a plurality of extensions of said housing in circular arrangement with spaces between them, each of said extensions having a tip which is of greater thickness than the remainder of said extensions.

11. The trephine instrument of claim 10, further comprising means for substantially preventing said extensions from bending toward each other during cutting.

12. The trephine instrument of claim 9, further comprising means for limiting travel of said piston relative to said means for cutting.

13. A method of cutting an annular hole into a bone with a trephine instrument, comprising a housing with a cutting face on a first end, a cannulated piston disposed within said housing and adapted for linear movement relative to said cutting face, and loading means resiliently urging said piston toward said first end, comprising the steps of:
securing a guide to the bone;
placing said trephine instrument over said guide through the cannulation in said piston;
rotating said trephine instrument and pressing it into the bone, thereby cutting a bone plug and pressing said piston into said housing against the urging of said loading means by said bone plug; and
removing said trephine instrument, said pressure of said piston against said bone plug helping to remove said trephine instrument cleanly.

14. The method of claim 13, further comprising, when it is desired to harvest said bone plug as a graft, the step of twisting said guide, thereby breaking the connection of said bone plug to the surrounding bone.

15. The method of claim 13, further comprising, when it is desired to treat a compression fracture in the area of said bone plug, the step of pressing the top of the bone plug, thereby causing the sections of bone on either side of the fracture to come together.

16. A trephine instrument for cutting an annulus into a material, which is accurately guided in a predetermined path through said material comprising:
a housing having a cutting face at a first end and comprising a plurality of prongs having cutting edges and spaces between said prongs whereby cut material accumulates in said spaces and escapes to the surface of said material through said spaces,
a piston disposed in said housing adapted for linear movement inwardly and outwardly of said first end of said housing, said piston having a head of approximately the same diameter as the inner diameter of said cutting face, whereby said piston head prevents said prongs from turning inward during cutting,
a cannulation in said piston to accommodate guide means; and
resilient means urging said piston toward said first end of said housing.

* * * * *

UNITED STATES PATENT AND TRADEMARK OFFICE
CERTIFICATE OF CORRECTION

PATENT NO. : 5,197,967
DATED : March 30, 1993
INVENTOR(S) : Frank Wilson

It is certified that error appears in the above—identified patent and that said Letters Patent is hereby corrected as shown below:

Col. 4, line 17,   change "ma" to --may--.

Col. 4, line 56,   change "out" to --cut--.

Signed and Sealed this

Eleventh Day of January, 1994

Attest:

BRUCE LEHMAN

Attesting Officer

Commissioner of Patents and Trademarks